United States Patent [19]

Bahl

[11] 4,351,901

[45] Sep. 28, 1982

[54] METHOD FOR SINGLE NUCLEOTIDE ALTERATION

[75] Inventor: Chander P. Bahl, El Cerrito, Calif.

[73] Assignee: Cetus Corporation, Berkeley, Calif.

[21] Appl. No.: 133,150

[22] Filed: Mar. 24, 1980

[51] Int. Cl.³ ............................................. C12N 15/00
[52] U.S. Cl. ....................................... 435/91; 435/68; 435/172; 435/317; 536/27
[58] Field of Search ......................... 435/172, 317, 91; 536/27

[56] References Cited

U.S. PATENT DOCUMENTS 4,264,731 4/1981 Shine .................................... 435/91
4,293,652 10/1981 Cohen ............................... 435/91 X

OTHER PUBLICATIONS

A. Razin et al., Proc. Nat'l. Acad. Sci. USA, 75(a), 4268–4270, (Sep. 1978).

C. Hutchison et al., J. Biol. Chem., 764, 6551–6560, (1978).

Primary Examiner—Sidney Marantz
Attorney, Agent, or Firm—Fitch, Even, Tabin, Flannery & Welsh

[57] ABSTRACT

A method for altering a single nucleotide at a predetermined position in a gene. The method involves the isolation of a single strand gene fragment extending up to the position before the nucleotide to be altered. A ribonucleotide or a protected deoxyribonucleotide corresponding to the desired altered nucleotide is attached at the end of this fragment. The fragment is then annealed to a complementary template which extends beyond the end of the fragment. The fragment is then extended complementary to the remainder of the template. The resulting partially mismatched double-stranded DNA is used to produce a pure DNA gene containing an altered deoxyribonucleotide at the single desired position.

18 Claims, 6 Drawing Figures

METHOD FOR SINGLE NUCLEOTIDE ALTERATION

This invention relates to molecular biology and the art of recombinant DNA and, more particularly, to a method for altering a nucleotide at a predetermined position in a gene.

As is well known, the double helix structure of DNA contains two interwound and complementary strands of nucleotides linked end to end. These nucleotides, of which there are four kinds in DNA (cytosine, guanine, adenine, and thymine; which are abbreviated, C, G, A, and T, respectively), encode the genetic message contained in each of the strands in accordance with the sequence in which the nucleotides are arranged. The strands of a DNA molecule are complementary because a given nucleotide on one strand is always opposite a specific nucleotide on the other strand. For example, C and G are always opposite, as are A and T. Thus, the sequence CATTACTAG lies immediately opposite a complementary sequence GTAATGATC on the other strand.

The deduction of the structure of the DNA molecule in the 1950s significantly increased the understanding of the biological processes called replication and translation. When DNA reproduces (the replication process), the helical double strand DNA unwinds and separates and a new chain of nucleotides forms next to each of the unpaired strands. These new chains or strands are each complementary to a respective one on the original unpaired strands. When the replication of each entire strand is complete, two new strands are formed in addition to the respective original unpaired strands they complement thus resulting in the production of two new double helices identical with the original DNA.

The process by which a living organism produces protein is termed translation. A protein is an assembly of amino acids in a specific linear sequence. Different proteins have different amino acid sequences. The particular sequence of amino acids in a given protein is determined in accordance with the code carried in the gene for that protein. Each gene is a segment of DNA wherein a series of nucleotides (nucleic acid components) is arranged in a particular order. Groups of three nucleotides encode specific amino acids, each group of these nucleotides being called a codon. Each codon specifies a particular amino acid in the protein molecule which the gene encodes. In the process of translation by which proteins are formed, each codon places one of twenty possible amino acids at a corresponding position in the protein chain.

Genetic change can occur randomly as a result of mutations appearing in a gene. As a result of a change in the gene, a corresponding change may occur in the protein which it encodes, changing the resultant properties of the organism. With the advent of recombinant DNA techniques, such genetic changes may be made deliberately by the introduction of a known nucleotide sequence from one strain or species into another. The known nucleotide sequence may be selected to confer a desired property upon the strain or species into which it is introduced. When the modified strain or species proceeds with the normal replication process, it also then duplicates the inserted sequence.

Recombinant DNA techniques involve isolating a suitable piece of a DNA chain (a vector or cloning vehicle) and breaking or severing the two strands of DNA of a cloning vehicle at the desired location where the foreign DNA is to be inserted. To do this, particular types of proteins, called restriction enzymes, are typically used. Certain restriction enzymes will break the DNA at particular nucleotide sequences, although the break may not necessarily occur at the same point on the two intertwined DNA strands. If two different types of DNA are severed in a similar manner, the open ends will therefore be complementary and will, under suitable conditions, stick together with the complementary ends lying side by side. This makes it possible to recombine two DNA segments from any source into a single DNA molecule.

All DNA, whether from microbes or from complex plants or animals, consists of the same set of nucleotides. Thus, when a DNA fragment derived from a foreign source is spliced into the DNA of a given species, the replication system of the host reproduces the inserted segment along with the DNA of the original host.

Once the DNA cloning vehicle has been isolated and the foreign piece inserted therein, the recombinant DNA is then placed into a suitable host organism. In order for the host organism to replicate the inserted DNA, it is necessary that the recombinant DNA be inserted into the host in such a way as to become part of its genetic system.

If the heterologous DNA is inserted in the cloning vehicle in the correct reading frame, it will not only be replicated, but it will express, that is, it will produce the protein encoded by the sequence of nucleotides in the gene. The process of producing proteins will result in the host cell producing the protein encoded by the heterologous DNA. The potential benefits are substantial and include, for example, the production of useful hormones such as human insulin.

A major difficulty in the use of recombinant DNA techniques for the production of desired protein is in isolating or cloning the gene which encodes production of the desired protein. This is particularly true where the gene desired is a human gene, for example one encoding production of a hormone such as insulin. It is possible where the amino acid sequence of a particular protein is known to synthesize a gene for its production. However, synthesis of a gene can be a lengthy and laborious technique. Moreover, many laboratories do not have the facility nor the trained personnel to take advantage of gene synthesis techniques.

In some cases, a gene which has already been cloned may differ structurally from an uncloned or difficult to clone gene by only one or a few bases or nucleotides. For example, animal insulin differs from human insulin in most cases by only one to several amino acids. Although animal insulin is taken by most diabetics, some patients do suffer immunological responses as a result of the amino acid differences, making it desirable to be able to supply human insulin to those individuals. If an animal insulin gene, such as rat insulin, could be altered at the specific nucleotides in the gene which differ from the corresponding nucleotides in human insulin so as to change the animal gene nucleotides to those present in the human gene, the resulting changed gene could be used to produce the human type of insulin. Other examples do exist where an already isolated or cloned gene may differ from an uncloned gene by only one or a few nucleotides.

Some methods are known for site specific nucleotide alteration. Some of these require chemical synthesis of short oligonucleotides. The others which alter the existing DNA segment can only alter a purine to another purine or a pyrimidine to another pyrimidine.

It is an object of the present invention to provide a method which makes it possible to alter a gene which has already been cloned, and which is similar but not identical to a desired but uncloned gene, so as to create the desired gene.

A more specific object of the invention is to provide a method for altering a gene at an individual nucleotide to change that nucleotide to a desired nucleotide.

A more general object of the invention is to provide an improved method for cloning genes.

A further object of the invention is to provide a partial hybrid double-stranded DNA-RNA structure useful as an intermediate product in recombinant DNA techniques.

Other objects of the invention will become apparent to those skilled in the art from the following description, taken in connection with the accompanying drawings wherein FIG. 1 illustrates a double stranded segment of DNA that will be cut by specific restriction enzymes at the sites shown by the arrows in that figure.

Very generally, in the method of the invention a nucleotide at a predetermined position in an available DNA sequence is altered. The alteration is such as to change the sequence of the available DNA to produce a desired DNA sequence such as a gene, initiation site, stop signal or restriction site. The alteration is accomplished as described below by isolating single strand fragments of the gene, each having a substantial number of bases on the 5' side of the predetermined position and terminating with the base immediately prior to the predetermined position. A ribonucleotide or a protected deoxyribonucleotide corresponding to the desired altered nucleotide is attached to each of the isolated fragments at the predetermined position. Single strand templates of DNA are provided, each corresponding to at least a portion of the strand of the gene complementary to the strand having the isolated fragment. The templates each have a first part complementary to the isolated fragments and a second part extending at least a substantial number of bases past the predetermined position. The isolated fragments are annealed to the first parts of the templates and are extended beyond the predetermined position complementary to the second parts of the templates. The resulting partial mismatched double strands may then be used to produce pure DNA containing altered deoxyribonucleotides at the predetermined positions.

The method of the invention will now be described in greater detail with reference to FIGS. 1 through 5 and 6. The FIGURES are schematic representations of successive steps in the general method of the invention applicable to any gene. Thus, in FIG. 1, the solid upper horizontal line represents one strand (the Watson strand) of a typical piece of double-stranded DNA which may constitute a part of chromosomal DNA, plasmid DNA, or phage DNA. The lower strand illustrated by the dotted line 13 represents the strand complementary to the strand 11 (the Crick strand). As is known, each strand is comprised of a series of nucleotides, joined together in succession. The particular position on the molecule at which the binding takes place is, as is known in the art, either the 5' position or the 3' position, dependent upon what is sometimes referred to as the upstream direction or the downstream direction of the molecule. For purposes of explanation herein, the 5' side of each nucleotide will be regarded as left-hand side in the upper strand 11 and the right-hand side in the lower strand 13. The 3' and 5' ends or directions are then on the opposite sides of the nucleotides, respectively, and in opposite orientation in the respective strands.

Figure 1:
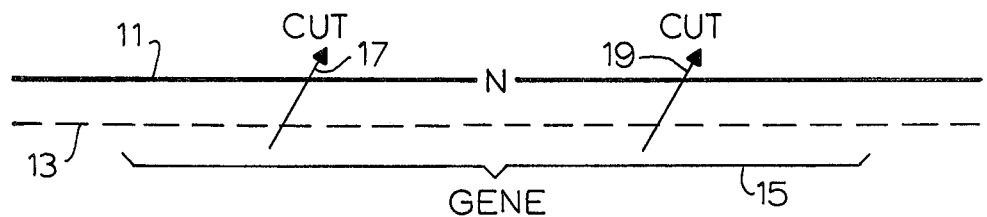

In FIG. 1, the nucleotides, in the double strands 11 and 13, which constitute a particular gene of interest are represented as being within the bracket 15. For purposes of explaining the general method of the invention, it will be assumed that the gene represented by the bracket 15 contains a single nucleotide N in the Watson strand 11 which is different from the structure of the desired uncloned gene. The invention, however, is applicable to situations where the differences are more than in a single nucleotide and the method of the invention may be repeated for each nucleotide desired to be altered until the alteration is complete. Naturally, the more nucleotides which are different in the cloned gene from those of the desired uncloned gene, the less convenient the method of the invention becomes. Nevertheless, the invention provides a powerful tool in situations where the differences between the nucleotides in the cloned gene and in the desired uncloned gene are only one or several.

In practicing the method of the invention, a small fragment containing the codon N to be changed is isolated. This is accomplished by cutting the DNA at positions that bracket the site of the nucleotide to be altered utilizing restriction enzymes. The two cut positions are illustrated schematically by the arrows 17 and 19 in FIG. 1. The action of restriction enzymes, and the particular sites in a gene at which they cut, are well known to those skilled in the art.

It is preferable but not crucial that the restriction enzymes be chosen to cut as closely to the base or nucleotide N to be altered as is possible. A substantial number of bases should be left on the 5' side or upstream side (the left side of N in the upper strand of FIG. 1) as is necessary to permit the single strand fragment, produced by later steps in the method of the invention, to anneal to a complementary template and to allow reverse transcriptase extension on the template. Typically, this will be at least about 8 to 10 bases; but it is conceivable that less would be sufficient. On the downstream or 3' side of the nucleotide N to be altered, the restriction site 19 utilized preferably should leave about 8 to 10 bases below or on the downstream side of the nucleotide to be altered as the upstream cut 17. However, in some rare instances it may be possible to cut at the 5' or upstream side of the nucleotide to be altered, thus eliminating several intermediate steps as discussed below.

Figure 2:
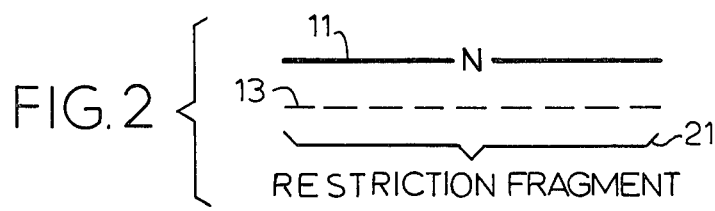
FIG. 2 illustrates the double stranded restriction fragment obtained after the cuts diagrammed in FIG. 1 have been made.

Referring now to FIG. 2, it may be seen that the cuts at 17 and 19 of the gene 15 in FIG. 1 result in a restriction fragment 21 having a double strand comprising the cut sections of the strands 11 and 13. It may also be seen that the strand 11 contains the nucleotide N at the position at which it is desired to alter. In most situations, the enzymes utilized to provide the cuts at 17 and 19 in FIG. 1 will cut in other places on the double-stranded DNA, resulting in a number of pieces of different sizes. As is known in the art, the correct or desired restriction fragment 21 may readily be selected by running the fragments on a polyacrylamide or agarose sizing gel. Fragments may be selected from the sizing gel which are of the appropriate length corresponding to the desired restriction fragment 21. To allow tracing of the molecule in future steps of the method, it is preferred that the 5' or leading ends of the restriction fragments be labeled with a radio isotopic phosphorus or the like placed in the phosphate groups which are part of the DNA. This may be done, as is known in the art, using a polynucleotide kinase.

The double-stranded restriction fragment 21 of FIG. 2 is then separated by any suitable technique known in the art. The individual single strand restriction fragments corresponding to the strand 11 and containing the nucleotide N to be altered are then selected, resulting in the single strand restriction fragment 23 shown in FIG. 3. Selection of the proper single strands is carried out by any suitable manner known in the art. For example, because of their different base compositions, two complementary strands will typically separate during electrophoresis, after denaturation, on a neutral polyacrylamide gel. Hayward, *Virology*, 49: 342. They can be easily excised and extracted. Aliquots of each strand can then be partially sequenced by any of a number of techniques, such as that of Maxam and Gilbert, *PNAS* 74: 560, to identify a desired strand.

Figure 3:
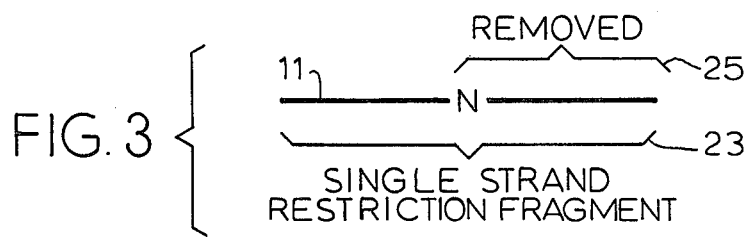
FIG. 3 is a representation of the single stranded restriction fragment obtained after separation of the double stranded restriction fragment shown in FIG. 2.

At this point in the method of the invention, the single strand fragments or Watson strand fragments 23 of the gene which have been isolated are treated so as to remove all of the bases or nucleotides which follow or which are on the 3' side of the nucleotide N to be altered and including the nucleotide N itself. The result is a single or Watson strand fragment of the gene which has a substantial number of bases on the 5' side of the predetermined position, N, and terminating with the base immediately prior to that predetermined position. The removed section is indicated in FIG. 3 by the bracket 25.

The portion 25 of the single strand restriction fragment 23 may be removed by any suitable means. For example, controlled exonucleolytic digestion may be used. It is preferred, however, to treat the single strand restriction fragment 23 in accordance with the procedures disclosed by Maxam and Gilbert, *PNAS*, 74:560. In this procedure, a strand is treated with dimethyl sulfate (a methylating compound) or hydrazine, or the like, specific for whichever base is to be altered, in a way resulting in partial cleavage of the fragments 23. This means that by appropriate treatment, such as sodium hydroxide and heat treatment, only those nucleotides at which a methylation or hydrazine reaction took place will be cut. This results in a number of different size pieces, including the total fragment (uncut). However, only a limited number of these fragments will contain the leading or 5' end of the single strand restriction fragment 23 of FIG. 3. As the latter end has been labeled, a first or rough selection of the resulting fragments may be obtained.

By way of example, if the base or nucleotide N to be replaced happens to be an adenosine, methylation may be utilized by treatment with dimethyl-sulphate at a certain frequency such that not all adenosine bases will be methylated in any one fragment. The strands are then cut by heat treatment in combination with a 0.1 M alkali treatment at 90° C. wherever a methylation took place. This may result in a large number of different size pieces. However, only a limited number of these pieces will include the leading or 5' ends of the original single strand restriction fragment 23. By appropriately labeling the leading ends, these latter pieces may be selected.

At this point, the method of the invention results in a population of single strand fragments of varying lengths, only one length of which is desired. Any suitable means may be utilized for selecting the single strand fragments of the desired length. However, a preferred technique is to utilize a polyacrylamide gel in accordance with the sequencing procedures of Maxam and Gilbert, supra with some modification. Although the Maxam-Gilbert gel has been considered used as an analytic technique, it is possible to utilize this technique preparatively by using a much higher amount of DNA than prescribed for analytical techniques. A manner in which this may be done is set forth in Example I, below.

Figure 4:
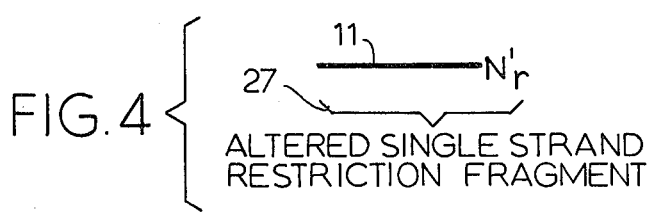
FIG. 4 represents the altered single stranded restriction fragment obtained following addition of a single ribonucleotide to the isolated gene fragment.

At this point in the method of the invention, the single strand restriction fragment from the strand 11 absent the removed section 25 is altered by the addition of a single ribonucleotide at the 3' end. The ribonucleotide added is the ribonucleotide which corresponds to the deoxyribonucleotide to which the particular nucleotide N of interest is to be changed. The nomenclature $N'_r$ is utilized, as shown in FIG. 4, to designate the single added ribonucleotide and the resultant altered single strand restriction fragment is illustrated therein as 27.

The reason that a ribonucleotide is attached in the foregoing step, rather than a deoxyribonucleotide, is that presently known techniques make it readily possible to add only a single base where the base is a ribonucleotide, whereas the addition of a single deoxyribonucleotide may be more difficult, and may require complex synthesizing techniques not readily available in a typical laboratory. More particularly, the addition of ribonucleotides may be readily accomplished by means of the enzyme terminal transferase and the appropriate nucleic acid. Such treatment will typically add 1 to 6 ribonucleotides to the 3' end of the fragments. (The use of terminal transferase in the presence of deoxyribonucleic acid typically results in the addition of far greater numbers of deoxyribonucleotides, giving inconvenient long strands instead of just a few bases). The ribonucleotides thus attached beyond the first one may be readily removed by treatment with alkali. This is because the first ribonucleotide is attached to a 3' deoxyribonucleotide and thus forms an alkali resistant bond (as does a deoxyribonucleotide). Unlike deoxyribonucleotides, however, subsequent ribonucleotides in the chain are attached to other ribonucleotides and consequently are alkali labile (as are the bonds of typical RNA) and thus may be severed by treatment with an alkali followed by alkaline phosphatase treatment to remove the 3' phosphate. After such treatment, relabeling with a radioactive phosphate may again be accomplished by kinasing onto the 5' end of the altered single strand restriction fragment 27.

As an alternative to adding a ribonucleotide to the single strand restriction fragment, it is possible to use a modified deoxynucleotide in which 3'OH has been substituted by a group which can be converted into a 3'OH. Such a group may be a 3' phosphomonoester. It is known that a 3'—OH on the added nucleotide is not necessary for the terminal transferase action since 2'-3' deoxynucleotide triphosphates have been used as substrates for addition of a single nucleotide at the 3' end of a DNA chain. These compounds cannot be extended further.

Figure 5:
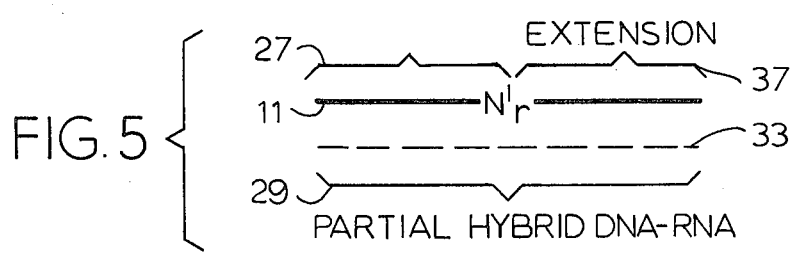
FIG. 5 illustrates a partial hybrid double stranded DNA-RNA linear fragment.
Figure 6:
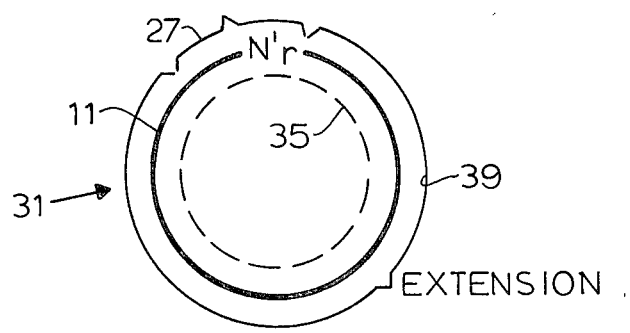
FIG. 6 illustrates an alternative, circular form of the double stranded DNA-RNA hybrid shown in FIG. 5.

In accordance with the invention, there is now formed a partial hybrid DNA-RNA fragment 29 as shown in FIG. 5, or a partial hybrid DNA-RNA loop as shown in FIG. 6. This is accomplished by providing a template fragment 33 (FIG. 5) or a template DNA loop 35 (FIG. 6). In either case, the template fragment 33 or the template loop 35 corresponds to at least a portion of the Cricks strand 13 (FIG. 1), that is, the strand of the gene complementary to the strand having the isolated fragment 27. Where a fragment template 33 is used, the template should start at the same position as the altered single strand restriction fragment. To do this, the gene 15 as shown in FIG. 1 may be cut at 17 and 19 and the Cricks strand or strand 13 separated and retrieved, or the downstream cut may be made further to the right from 19 in FIG. 1. In any case, the resulting template has a first part which is complementary to the isolated fragment or altered fragment 27 and has a second part extending at least a substantial number of bases past the predetermined position opposite $N'_r$. The altered single strand restriction fragment 27 is then annealed to the template 33 or 35 at the appropriate complementary positions. Naturally, the nucleotide in the template 33 or 35 at the normally complementary position to the position at which the $N'_r$ ribonucleotide is positioned will not be complementary to that ribonucleotide but will still be complementary to what was the deoxyribonucleotide originally at that predetermined position in the strand 11.

At this point in the method of the invention, the altered single strand restriction fragment 27 is extended a substantial number of bases past the predetermined position, that is, the position of $N'_r$ complementary to the second parts of the templates 33 or 35. This is preferably accomplished using reverse transcriptase as the polymerase because it lacks the "proofreading" function of some polymerases like E. coli DNA polymerase I, and will leave unaffected the unpaired mismatch at the position of $N'_r$.

It is preferable to add the initial few bases one at a time and subsequently check to see if the addition has actually taken place. This is because in using the sequencing gel in accordance with the Maxam-Gilbert technique previously discussed for isolating the single strand restriction fragments with the removed portions 25, more than one type or size of fragment could exist unseen in the single band cut out of the gel. This could occur, for example, if one of the unlabeled fragments made by the partial fragmentation treatment comigrated on the gel with the desired fragment. Such an occurrence cannot be readily predicted because migration depends upon base composition as well as on length, and varies with the exact conditions under which the sequencing gel is utilized. By checking the addition of each of the first several nucleotides one at a time, any contaminants will be readily discovered and eliminated. This is because the contaminant will be annealed at complementary positions on the strand 33 or loop 35 at different positions than the correct fragment 27. Accordingly, after the addition of one or a few bases, the improper complementation existing in the template will come into play resulting in a failure of the particular base to be added. Thus, by monitoring incorporation for several bases, the purity can be ascertained. If there is a contaminant, then running the fragments on a gel under slightly altered conditions should separate the fragments, as they are very sensitive to conditions.

Once purity is ascertained, the remaining deoxyribonucleotides necessary to obtain the full extension 37 is completed. In the case of the loop of FIG. 6, the extension 39 continues around the full loop. The result in either case is a partial hybrid DNA-RNA fragment or loop containing a single ribonucleotide at the predetermined position.

The resulting partial hybrid double-stranded DNA-RNA is used to produce a pure DNA gene containing an altered deoxyribonucleotide at the predetermined positin. To do this, there are several possible techniques. One technique would be to transform with the partial hybrid into a bacterial cell carrying the original unaltered gene. A second method is to separate the partial hybrid strands and isolate the strand without the ribonucleotide in it and use that isolated strand as a template. The resulting double-stranded DNA may then be used in vivo and the desired progeny selected, or may be further separated and the non-template strand used as a further template. A further technique, possible in the case of the circular loop of FIG. 6, is to digest the template 35 and use the remaining single loop, containing the single ribonucleotide, as a template.

Although transformation with the fragment in a bacterial cell carrying the original gene appears to be the shortest technique, it also has the lowest probability of success in a given experiment. This is because cell carried enzymatic systems tend to correct mismatches such as the RNA-DNA mismatch in the altered single strand restrictin fragment. Because the base which is desired is a ribonucleotide, the normal cell mechanisms may remove that mismatch as opposed to the non-paired but more analogous deoxyribonucleotides.

A more reliable method is the separation method followed by use of the corrected strand as a template. The strands 11 and 33 or 11 and 35 are separated and the corrected strand containing the $N'_r$ nucleotide is used as a template. Use of reverse transcriptase will then add a complementary strand of DNA in which the base complementary to the $N'_r$ position is deoxyribonucleotide. Such a fragment or loop may then be transferred to a bacterial cell and transformed. Such a procedure is particularly useful if a way exists for strongly selecting transformed genes. Such ways could include immunological techniques selecting for the gene product.

In the absence of strong selection techniques, the added DNA strand containing only deoxyribonucleotides can be used to correct the gene in vitro. In one approach, an entire plasmid carrying the original unaltered gene is cut with a suitable restriction enzyme and linearized. The separated strands are then recircularized. The altered single strand restriction fragment is then annealed to the complementary single circular strand and is extended (at 37) by the foregoing described reverse transcriptase technique. The plasmid is then used as a cloning vector in a suitable bacterial host.

As an alternative, the plasmid can be nicked (cut in one place and in one strand only, by known restriction enzyme techniques). Once a nick results, the supercoiled condition of the DNA double helix is relaxed and it is possible, through the use of appropriate enzymes, to digest the nicked fragment. The resulting single-stranded intact loops may then be used as templates for extension of the altered single stranded restriction fragments.

At this point, two possible means exist for isolating the corrected gene. The plasmid may be placed in a cell and the cell allowed to replicate. Proper selection or screening can be utilized to obtain the desired clones. Alternatively, the plasmid with the single corrected DNA strand can again be linearized and the strands separated. The fragments still carrying the radioactive labels at this point may be readily identified. Priming with any small fragment not in the corrected region and suitable extension with a polymerase can result in a pure population of plasmids carrying the corrected gene.

EXAMPLE I

The gene for rat insulin has been cloned, Gilbert et al., *PNAS* 75:3727 and Ullrich et al., *Science* 196:1313. Rat insulin differs from human insulin in several places. Some of these places are in the pre-pro-insulin and in the pro-insulin C chain. The natural biological processing of such forms into the final form of active insulin, however, results in removal of the pre-pro-insulin and in the pro-insulin C chain. The only differences in active human insulin and active rat insulin are in the A and B chains. There are three amino acids in the rat B chain and one amino acid in the rat A chain that distinguish rat insulin from human insulin. More particularly, the third amino acid of the B chain of the rat insulin sequence is lysine (coded for by the codon AAA in the gene). In human insulin the corresponding amino acid is aspargine. Position 9 amino acid in rat insulin is proline (coded by CCT) whereas in human insulin it is serine. In position 30 of the B chain of the rat insulin sequence is serine (coded for by the codon UCC). In human insulin the corresponding amino acid is threonine. In the A chain of the rat insulin sequence, the fourth position is aspartic acid (coded for by the codon GAT in the gene). In human insulin, the corresponding amino acid is glutamic acid. Thus, if the four different codons can be altered, the cloned gene for rat insulin may be changed to a gene coding for human insulin. Even though the resulting gene is not the same as the human insulin gene, the resulting product is the same.

By examining the genetic code, it may be determined that all four of the necessary alterations to change the gene coding for rat insulin to a gene which produces human insulin may be accomplished by changing a single base in each codon. Thus, the codon AAA can be changed in its last position to a T or a C forming AAT or AAC which codes for aspargine. The codon CCT can be changed to TCT to code for serine. The codon TTC can be changed in the first position to ATC and it will code for threonine. The codon GAT can be changed in the third position to GAA or GAG in order to code for glutamic acid. Thus, by altering each of the three codons at a single specific nucleotide, the rat insulin gene may be altered to one coding for human insulin.

In changing the cytosine to adenosine at the third position in the B chain, a small fragment containing the codon to be changed is isolated. In this particular case, double digestion by *Hae* III and *Ava* II will accomplish this inasmuch as there is a *Hae* III site in the pre-insulin chain and an *Ava* II site 15 nucleotides beyond the desired alteration. There are other places where these enzymes cut but separation may be readily accomplished on a suitable sizing gel. *Hae* III cuts in the pre-insulin regin 38 nucleotides from the start of the B chain coding sequence, and *Ava* II cuts at the 24th nucleotide of the B chain coding sequence. Thus, the fragment from the sizing gel, which runs at approximately 62 bases long, will be the desired piece. *Hae* III restriction conditions used are those of Bron and Murry *Mol. Gen. Genet.*, 143:25. *Ava* II restriction conditions used are those of Murray, et al., *Biochem. J.*, 159:317. *Mbo* II restriction conditions are those of Endow, *J. Mole. Bio.*, 114:441.

The 5' ends are labeled with $^{32}p$ using polynucleotide kinase. $^{32}p$ is a radioactive phosphorous atom, placed in the phosphate groups which are part of DNA, to allow tracing the molecule in future steps.

Labeling of DNA with $^{32}p$ is done as follows: oligonucleotides (200 p mol) in 50 microliters of solution containing 66 millimolar Tris HCL (pH 7.8), 6.7 millimolar magnesium chloride ($MgCl_2$), 15 millimolar Dithiothreitol and 66 micromolar [$^{32}p$] ATP is incubated at 37° with 2 to 4 units of T4 polynucleotide kinase for 40 minutes. The reaction is terminated by the addition of excess EDTA, and 5' $^{32}p$ labeled olgonucleotides are purified and desalted on a Sephadex G-50 column (fine) using 0.1 molar triethalammonium bicarbonate (pH 8.0) as buffer.

The adenosine residues are methylated by treatment with dimethyl sulphate following the procedure of Maxam and Gilbert *PNAS*, 74:560. Heat treatment followed by 0.1 M alkaline treatment at 90° C. cuts the strands wherever a methylation takes place. Since there are nine places where cuts might occur, 52 different sized pieces, including the uncut strands and not counting single adenosine nucleotide fragments. Only ten of the 52 fragments will include the labeled 5' end. A Maxam-gilbert sequencing gel is then utilized in accordance with the published technique. An alteration in procedure, however, is made as follows: Fifty times the prescribed DNA is used for reactions, and the specific activity of the ATP label is therefore fifty times less than given (60 ci/mmol. instead of 1200 ci/mmol.). Thus, the need for carrier is eliminated. This is important in using the gel preparatively, rather than analytically. The bands are eluted from the gel as follows: In siliconized scintillation vials the gel slices are ground to a paste. 0.75 mls of buffer (10 mM TRIS HCl, pH 7.8), 0.5 molar ammonium acetate, 0.01 molar magnesium acetate, 0.1% SDS, and 0.1 millimolar EDTA are added. The vials are incubated at 37° for 10 hours. They are then centrifuged, and rinsed with fresh buffer and alcohol precipitated two times.

The methylation cleavage reaction leaves a phosphate at the 3' end molecule. The phosphates at both ends are removed with an alkaline phosphatase such as BAP and the $^{32}p$ phosphate is kinased back on the 5' end.

Alternatively, the 3' phosphate can be specifically removed by treating with kinase in the absence of ATP Cameron et al., *Biochem.*, 16:5120.

Next the fragments are treated with the enzyme terminal transferase in the presence of uridine (or ribocytidine). The conditions followed are those of Roychoudhuri et al., *Nucleic Acid Research*, 3:863. This treatment adds 1 to 6 uridine nucleotides to the 3' end. Treatment with alkali removes all but the first one of the uridine nucleotides leaving a phosphate at the 3' end. BAP treatment is once again utilized to remove the phosphates as in Roychoudhuri, supra, and a labeled phosphate is once again kinased onto the 5' end.

A second restriction fragment is then isolated, this one starting at the same place, the Hae III cut, but extending further downstream. A convenient site to terminate this piece is the Mbo II site about 50 nucleotides downstream. The strands are then separated and the non-coding strand isolated. This non-coding strand is the sequence complementary to the initially isolated strand. At this point the two are annealed together and the shorter fragment is extended using reverse transcriptase treatment as described in Bahl et al., PNAS, 74:3240. A gene having the correction in pure DNA is then developed as described above and the procedure is repeated at the other three areas to obtain the desired gene.

EXAMPLE II

Two other examples of useful nucleotide conversions come from the hormone Pituitary Adrenal Corticotrophin or ACTH. The gene for bovine ACTH has been cloned and sequenced. ACTH is made as part of a long polypeptide, including another hormone before it and two after it; these are cut by trypsin-like enzymes to yield the individual hormone.

Human ACTH differs from bovine ACTH at only one amino acid. Amino acid position 33 is glutamine in the bovine ACTH, and is glutamic acid in the human version. Glutamic acid can be coded for by GAG. Thus, the single specific nucleotide conversion creating GAG from CAG will suffice to create a sequence coding for ACTH. There are appropriate restriction sites available; EcoR1 and Xho 1 downstream and upstream an Ava II site in the nucleotide sequence coding for the proceeding hormone in the precursor form.

Thus, the method is totally identical to the insulin example, except for two things: First, slightly different restriction enzyme digestion conditions must be used when a different enzyme is used. Ava II conditions are again those of Murray et al., Biochem. J., 159:317. But EcoR1 conditions are those used by Green, et al., Methods Mole. Bio., 7:87 and Xho conditions are those of Gingeras et al., J. Mole. Bio., 118:113.

Secondly, in the insulin example an adenosine base was changed, in this case, it is cytosine that must be altered (to guanosine). Therefore, instead of Maxam and Gilbert methylation/cleavage reaction, their hydrazine treatment followed by 0.5 molar piperidine cleavage is performed. Hydrazine treatment is in the presence of 2 molar NaCl to preferentially suppress the thymidine reaction. All this follows Maxam and Gilbert's procedure, PNAS, 74:560. Then the guanine base is added as rG with terminal transferase as described above.

A second example is to be found from the same hormone, ACTH. It is known that only the first 24 amino acids are necessary to provide the full biological activity of the hormone. Since bovine ACTH is identical to human ACTH for the first 32 amino acids, the first 24 codons of the bovine gene can be cloned to produce human ACTH activity. However, there is no enzymatic way to cut the protein at the 24th amino acid once the whole protein is made. Therefore, a "stop" codon (UAG, UAA, or UAG) must be inserted to terminate translation at that point.

The 25th codon is AAC (coding for aspargine). This can be altered to UAA by two base changes. The first is replaced by a U, using the same reactions as with insulin and the same restriction enzymes as listed above for the bovine ACTH conversion to total human form. Next, the procedure is repeated, again with the same restriction enzymes, but now replacing the cytosine with an adenosine or a guanidine nucleotide. Here the cleavage reactions specific for cytosine is again employed. At each step, the appropriate base is added as a ribonucleotide (rU or rA) with terminal transferase.

EXAMPLE III

Another example of a molecule that has been cloned which can be altered into a more useful form is bovine growth hormone (BGH). This hormone is similar to human growth hormone (HGH), the active fragment of the hormone differs from it in 13 out of 39 amino acids. HGH, in turn, is related to another human hormone, HCS. There are 10 amino acid positions where they differ. HCS differs from BGH by 17 amino acids. Using the method given, the cloned BGH gene can be converted to code for HGH, which can in turn be altered to code for HCS, or, if desired, the BGH gene can be altered directly to code for HCS. While the amino acids sequences are indeed known for all three, the nucleotide sequence of the cloned BGH has not yet been worked out. While this is a necessary prerequisite for the conversion, the success of such an experiment can be shown by examining all the possible codons for each amino acid. To show the potential of the technique, a few changes needed to produce HGH from BGH will be discussed.

The third amino acid in BGH is threonine. In human form, it is alanine. The codons for threonine are ACU, ACC, ACA and ACG. Those for alanine are GCU, GCC, GCA and GCG. Thus, no matter which codon occurs for threonine, it can be changed to a codon for alanine by converting the first base, A, to a G. This means using the method of Maxam and Gilbert specific for adenosine cleavage followed by treatment with terminal transferase in the presence of rG.

The second difference between the two is in amino acid position 8. BGH has a phenylalanine and HGH has a tyrosine at that spot. The codon for phenylalamine could be UUU or UUC. If it was UUC, a single base change of the second U to an A would produce UAC, which codes for tyrosine. And if the phenylalanine codon were UUU, a change of the middle U to an A would again give a tyrosine codon.

Similar single base changes will suffice for most of the differences. This is reasonable, since the hormone probably diverged, in evolutionary terms, by single base mutations. However, for instance, amino acid #13 in BGH is arginine. Four of the possible codons that could turn out to be there in the bovine gene are AGG, AGA CGG, and CGA. None of them have any bases in common with human aspartic acid codons, GAU or GAC. If the arginine codon is CGU or CGC, there would be one common base. However, the power of the technique is such that this will not matter. It merely necessitates running through the procedure two or three times, and substituting for each base in turn, one at a time.

It may be seen therefore, that the invention provides an improved method for cloning a desired gene or more generally a desired sequence of DNA. In addition for use in producing desired proteins, the method is useful for producing specific mutations or similar goals in research.

Various modifications of the invention in addition to those shown and described herein will become apparent to those skilled in the art from the foregoing description and accompanying drawings. Such modifications are intended to fall within the scope of the appended claims.

What is claimed is:

1. A method for altering a nucleotide at a predetermined position in a gene, comprising, isolating single strand fragments of the gene, each having a substantial number of bases on the 5' side of the predetermined position and terminating with the base immediately prior to the predetermined position, attaching a nucleotide corresponding to the desired altered nucleotide to each of the isolated fragments at the predetermined position, providing single strand templates of DNA each corresponding to at least a portion of the strand of the gene complementary to the strand having the isolated fragment, each template having a first part complementary to the isolated fragment and a second part extending at least a substantial number of bases past the predetermined position, annealing the isolated fragments to the first parts of the templates, and producing mismatched double-stranded DNA containing altered nucleotides at the predetermined position by extending the isolated fragments beyond the predetermined position complementary to the second parts of the templates.

2. The method of claim 1 wherein the attached nucleotide is a ribonucleotide.

3. The method of claim 1 wherein the attached nucleotide is a protected deoxyribonucleotide.

4. The method of claim 1 wherein the mismatched double-stranded DNA is used to produce pure DNA genes containing altered nucleotides at the predetermined position.

5. The method of claim 1 wherein said templates are circular pieces of DNA.

6. The method of claim 1 wherein said templates are DNA fragments having 5' ends corresponding to the 5' ends of said isolated fragments.

7. The method of claim 1 wherein said single strand fragments are isolated by first isolating double-stranded DNA gene fragments having a substantial number of bases on each side of the predetermined position, separating the strands of said double-stranded DNA gene fragments and isolating single strands thereof containing the nucleotide to be altered, and fragmenting the isolated single strands and selecting those having all the bases preceding but not including the predetermined position.

8. A method according to claim 7 wherein said fragmented isolated single strands are selected by electrophoresis on a polyacrylamide gel.

9. A method according to claim 7 wherein said single strands are fragmented by treatment with dimethyl sulfate or hydrazine followed by sodium hydroxide.

10. A method for producing a partial hybrid double-stranded mismatched DNA intermediate product, comprising, isolating single strand fragments of the gene, each having a substantial number of bases on the 5' side of the predetermined position and terminating with the base immediately prior to the predetermined position, attaching a nucleotide corresponding to the desired altered nucleotide to each of the isolated fragments at the predetermined position, providing single strand templates of DNA each corresponding to at least a portion of the strand of the gene complementary to the strand having the isolated fragment, each template having a first part complementary to the isolated fragment and a second part extending at least a substantial number of bases past the predetermined position, annealing the isolated fragments to the first parts of the templates, and extending the isolated fragments beyond the predetermined position complementary to the second part of the templates.

11. A method according to claim 10 wherein said desired single nucleotide is added by initially attaching between one and six ribonucleotides with the enzyme terminal transferase and then removing all but one by treatment with alkali.

12. A method according to claim 10 wherein said desired single nucleotide is added by attaching a single protected deoxyribonucleotide with the enzyme terminal transferase and then converting the protecting group to a 3'OH.

13. An intermediate product comprising a partial hybrid double stranded DNA-RNA wherein a first strand comprised solely of deoxyribonucleotides is annealed to a second strand having complementary deoxyribonucleotides except for a single ribonucleotide located at a position a substantial distance from the ends of said strand.

14. A method for producing a desired DNA sequence, comprising, selecting an available sequence of DNA substantially identical with said desired DNA sequence but differing from said desired sequence by at least one nucleotide, and altering said different nucleotides one at a time by the method of claim 1 until the desired sequence is achieved.

15. A method according to claim 14 wherein said desired sequence comprises a gene.

16. A method according to claim 14 wherein said desired sequence comprises an initiation sequence.

17. A method according to claim 14 wherein said desired sequence comprises a stop sequence.

18. A method according to claim 14 wherein said desired sequence comprises a restriction enzyme site.

* * * * *